US009149391B1

(12) United States Patent
Paolinetti

(10) Patent No.: US 9,149,391 B1
(45) Date of Patent: Oct. 6, 2015

(54) SAFETY GOGGLES WITH VENTILATING FANS

(71) Applicant: Kevin Paolinetti, Mount Shasta, CA (US)

(72) Inventor: Kevin Paolinetti, Mount Shasta, CA (US)

(*) Notice: Subject to any disclaimer, the term of this patent is extended or adjusted under 35 U.S.C. 154(b) by 0 days.

(21) Appl. No.: 14/590,611

(22) Filed: Jan. 6, 2015

(51) Int. Cl.
*A61F 9/02* (2006.01)

(52) U.S. Cl.
CPC ..................................... *A61F 9/028* (2013.01)

(58) Field of Classification Search
CPC .......... A61F 9/028; A61F 9/025; A61F 9/068
USPC ................... 2/436, 437, 438, 8.6; 128/201.15
See application file for complete search history.

(56) References Cited

U.S. PATENT DOCUMENTS

| 2,526,737 | A | * | 10/1950 | Farina | 2/436 |
| 3,015,987 | A | * | 1/1962 | Harrison | 2/436 |
| 3,825,953 | A | * | 7/1974 | Hunter | 2/437 |
| 4,150,443 | A | * | 4/1979 | McNeilly | 2/436 |
| 4,309,774 | A | | 1/1982 | Guzowski | |
| 4,443,893 | A | | 4/1984 | Yamamoto | |
| D359,502 | S | | 6/1995 | Hicks | |
| 5,452,480 | A | | 9/1995 | Ryden | |
| 5,542,130 | A | * | 8/1996 | Grabos et al. | 2/436 |
| 5,966,746 | A | | 10/1999 | Reedy | |
| 6,038,707 | A | | 3/2000 | Ryden | |

FOREIGN PATENT DOCUMENTS

KR          200451350 Y1    12/2009

* cited by examiner

*Primary Examiner* — Tejash Patel
(74) *Attorney, Agent, or Firm* — Kyle A. Fletcher, Esq.

(57) ABSTRACT

The safety goggles with a ventilation fan is an eye protection system intended to improve wearer safety and comfort by preventing fogging. The safety goggles with a ventilation fan comprises safety goggles, a ventilation fan, and a distribution system to direct airflow through the goggles.

12 Claims, 5 Drawing Sheets

SAFETY GOGGLES WITH VENTILATING FANS

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

The present invention relates to the field of personal protective equipment, more specifically, the invention is directed to eye protection goggles with a ventilation system.

People use safety goggles to protect their eyes in potentially hazardous situations. One drawback of safety goggles is their propensity to fogging. Fogging is a result of the condensation of water on the lens of safety goggles while the safety goggles are being worn. Goggles are prone to fog when body heat and body sweat accumulates in the space between a lens and a wearer's face. When a temperature differential between the ambient temperature (on the outside of the lens) and the temperature of the space between the lens and wearer's face exists, the cooler air will tend to cool the lens causing the water vapor in the warmer space to condense on the lens.

A second drawback of safety goggles is that when a temperature differential between the ambient temperature (on the outside of the lens) and the temperature of the space between the lens and wearer's face exists, the safety goggles can also become uncomfortable to wear. A third drawback of safety goggles is that excess water vapor, in the form of sweat, tends to accumulate in the space between the lens and wearer's face, which increases the propensity of fogging.

SUMMARY OF INVENTION

The purpose of the safety goggles with ventilation fan is to reduce this inherent fogging by reducing the temperature differential by pumping ambient temperature air into the space between the lens and wearer's face. This air flow reduces the temperature differential and helps to remove the excess water vapor in the space between the lens and wearer's face.

The safety goggles with a ventilation fan is an eye protection system comprising safety goggles, two independently controlled ventilation fans, and a distribution system to direct air flow through the goggles.

These together with additional objects, features and advantages of the safety goggles with a ventilation fan will be readily apparent to those of ordinary skill in the art upon reading the following detailed description of the presently preferred, but nonetheless illustrative, embodiments when taken in conjunction with the accompanying drawings.

In this respect, before explaining the current embodiments of the safety goggles with a ventilation fan in detail, it is to be understood that the safety goggles with a ventilation fan is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the safety goggles with a ventilation fan.

It is therefore important that the claims be regarded as including such equivalent construction insofar as they do not depart from the spirit and scope of the safety goggles with a ventilation fan. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principle of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
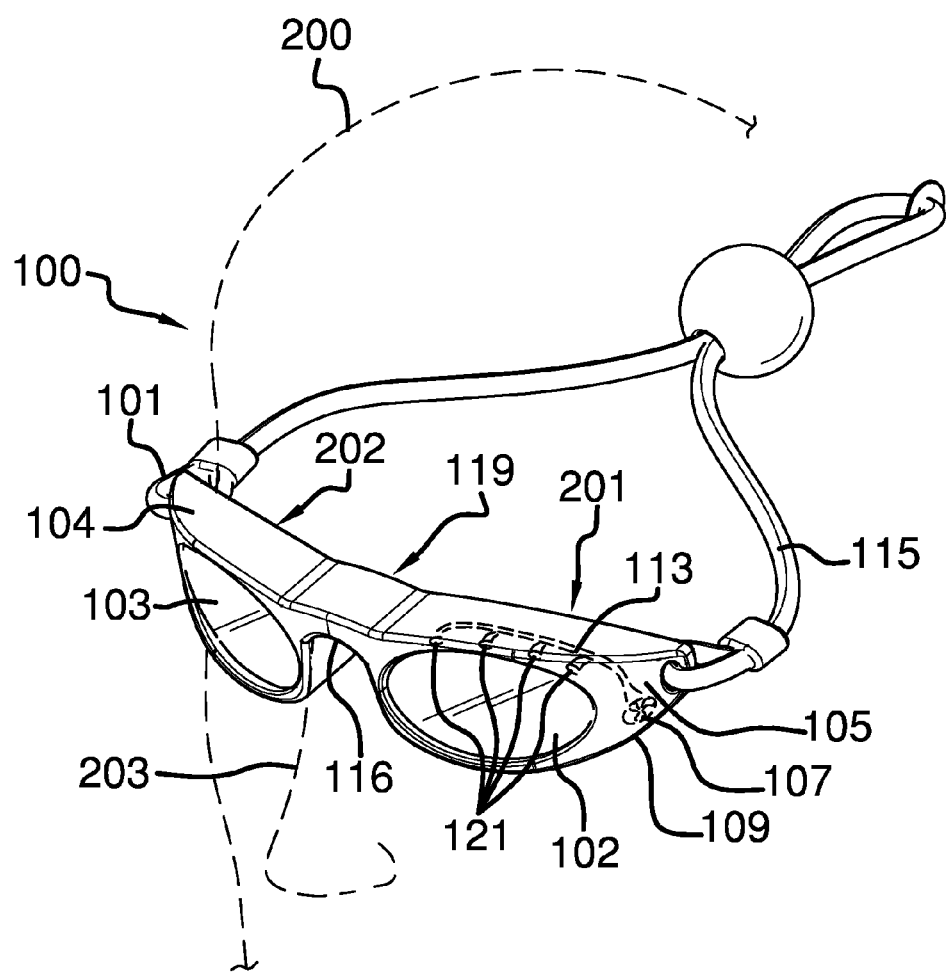
FIG. 1 is a front perspective view of an embodiment of the disclosure.
Figure 2:
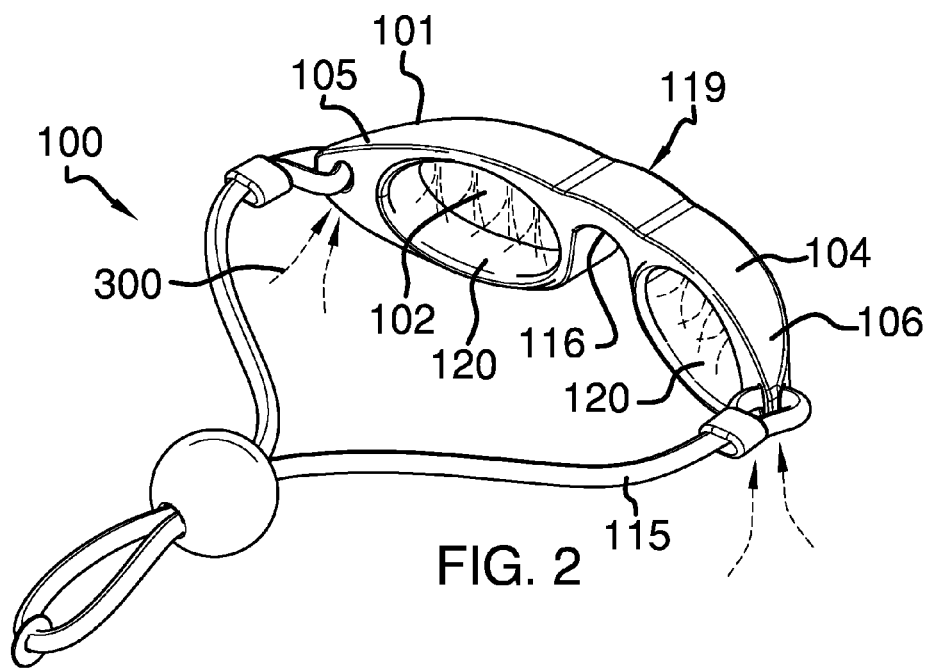
FIG. 2 is a rear perspective view of an embodiment of the disclosure.
Figure 4:
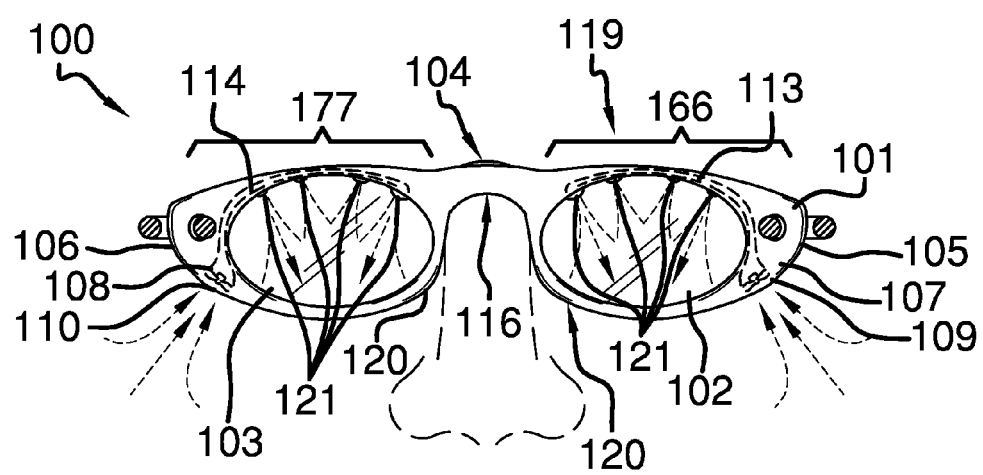
FIG. 4 is a front view of an embodiment of the disclosure.
Figure 3:
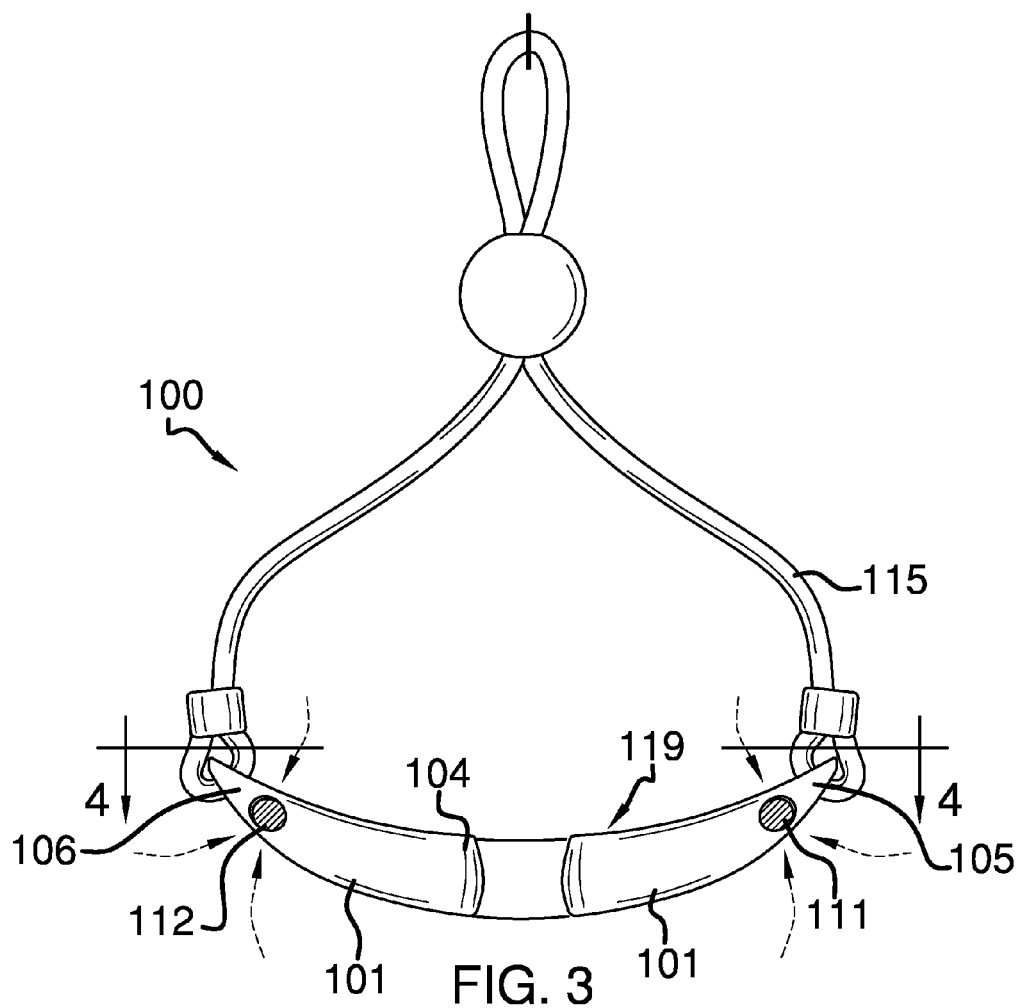
FIG. 3 is a bottom view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

In the specification and claims, the following definition will be used:

Safety Goggles: Safety goggles are forms of protective eyewear that enclose the area surrounding the eyes in order to protect the area surrounding the eye, and preventing particulates, liquids, or chemicals from striking the eye. Safety goggles are also used in cold weather activities to protect the eyes from the wind and cold from irritating the eyes. In this specification, the term safety goggles specifically intends to include the use of glasses, wearable eye shields, protective facewear or facemasks.

Detailed reference will now be made to potential embodiments of the present invention, examples of which are illustrated in FIGS. 1-6. The safety goggles with a ventilation fan 100 (hereinafter invention) is an eye protection system comprising safety goggles 119, a left side ventilation system 177, a right side ventilation system 166, a left side air tube 113 and a right side air tube 114.

The safety goggles 119 are comprised of a frame 101, a left lens 102, a right lens 103, a left side shield 105, a right side shield 106, and a bridge 116. The safety goggles may also include an top shield 104 as well as an bottom shield 120. The safety goggles 119 are worn so that the left lens 102 is adapted to protect a left eye 201 of a wearer 200, the right lens 103 is adapted to protect a right eye 202 of the wearer 200, and the bridge 116 is adapted to rest on a nose 203 of the wearer 200. When worn like this, the left side shield 105 protects the left eye 201 from impacts and debris coming from the left side of the wearer 200, and the right side shield 106 protects the right eye 202 from impacts and debris coming from the right side of the wearer 200. When used, the top shield 104 is adapted to protect the left and the right eyes 201, 202 from impacts and debris coming from above the wearer 200, and the bottom shield 120 is adapted to protect the left and the right eyes 201, 202 from impacts and debris coming from below the wearer 200.

Figure 5:
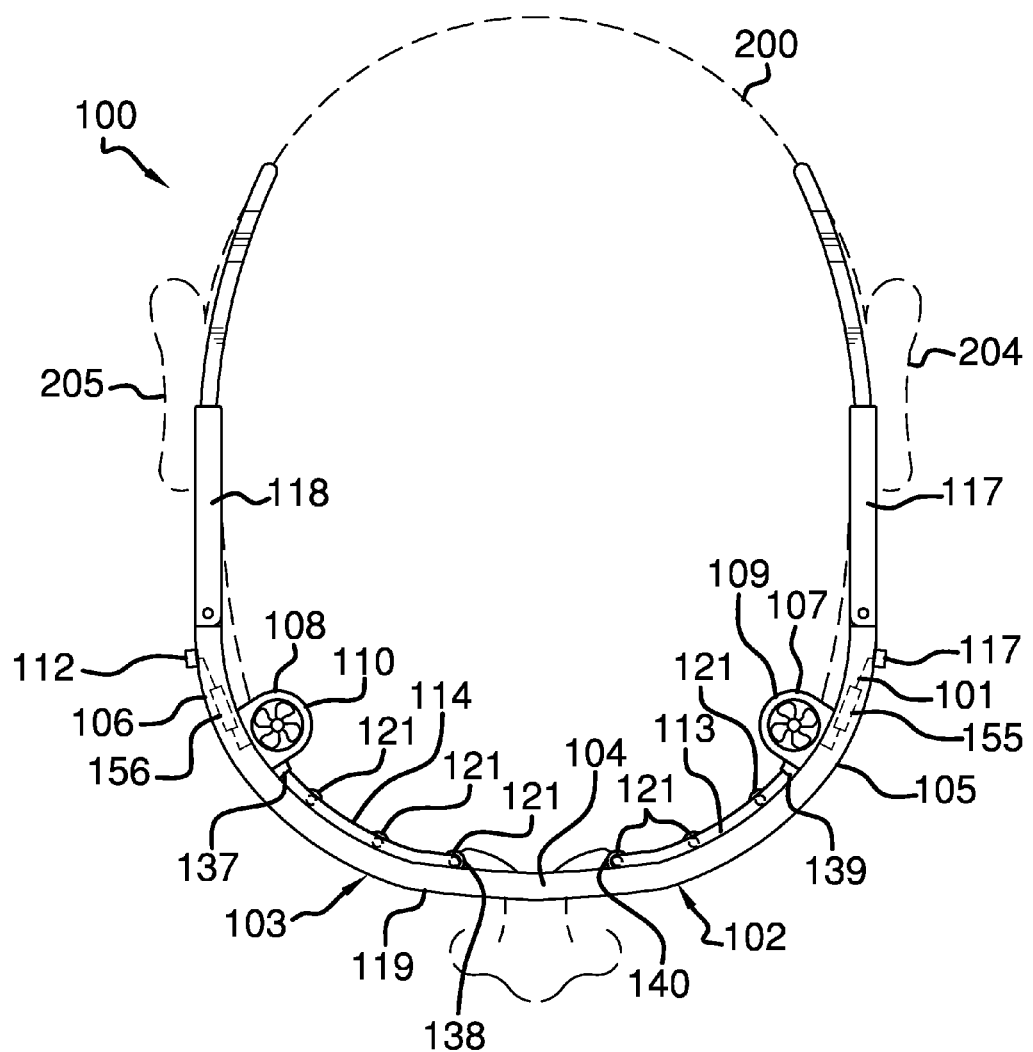
FIG. 5 is a top view of an alternative embodiment of the disclosure.
Figure 6:
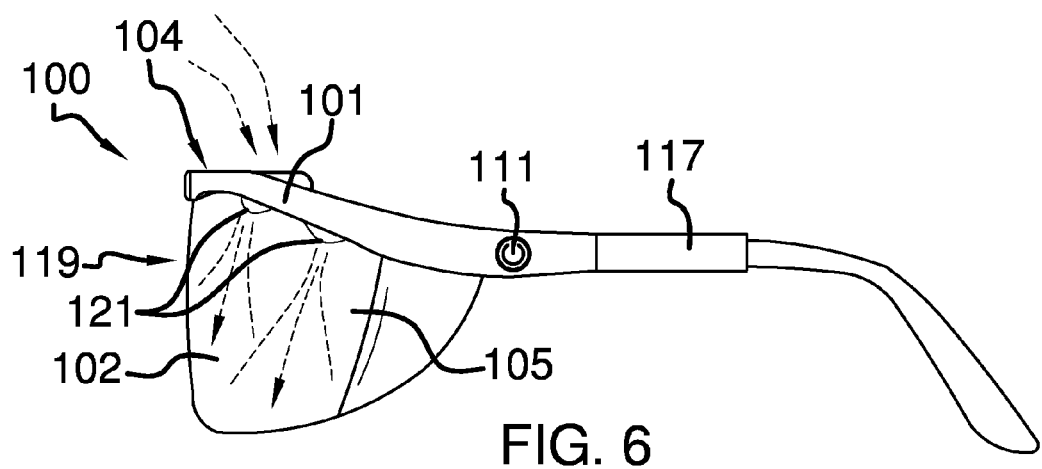
FIG. 6 is a side view of an alternative embodiment of the disclosure.

There are several methods to secure the safety goggles 119 to the wearer including, but not limited to, the use of a strap 115, or the use of a left temple 117 and right temple 118. The use of a strap 115 is exemplified in a first potential embodiment of the invention 100 that is illustrated in FIGS. 1 through 4. When the safety goggles 119 are equipped with a strap 115, the strap 115 is adjusted to provide enough tension to hold the goggles against the wearer. The use of the left temple 117 and right temple 118 is exemplified in a second potential embodiment of the invention 100 that is illustrated in FIGS. 5 and 6. When the safety goggles 119 are equipped with the left temple 117 and right temple 118, the left temple 117 is adapted to rest on a left ear 204 of the wearer 200, and the right temple 118 is adapted to rest on a right ear 205 of the wearer 200. When in used in this manner, the left temple 117 resting on the left ear 204 of the wearer 200, the right temple 118 resting on the right ear 205 of the wearer 200, and the bridge 116 rests on the nose 203 of the wearer 200 act as the resting points that hold the safety goggles 119 in place.

The purpose of the frame 101 provides a structure to which the left lens 102, the right lens 103, the left side shield 105, the right side shield 106, bridge 116, the top shield 104, the bottom shield 120, the strap 115 or left temple 117 and right temple 118 can be attached and held in place.

The left lens 102 and right lens 103 are made of polycarbonate. While the left lens 102 and right lens 103 may be tinted, the left lens 102 and right lens 103 will be transparent enough to allow the wearer 200 to see through the left lens 102 and right lens 103. If desired, the left lens 102 and right lens 103 may be formed to provide vision correction.

The choice of materials for use in the left side shield 105, the right side shield 106, the bridge 116, the top shield 104, the bottom shield 120, and, when used, the left temple 117 and right temple 118 depends on the intended use and design of the safety goggles 119, but are not limited to, polycarbonate or polyethylene. The left side shield 105, the right side shield 106, bridge 116, the top shield 104, the bottom shield 120 and, when used, the left temple 117 and right temple 118 may be molded as a single unit. When polycarbonate is used, the left lens 102 the right lens 103, the left side shield 105, the right side shield 106, bridge 116, the top shield 104, the bottom shield 120 and, when used, the left temple 117 and right temple 118 may be molded as a single unit.

The left side ventilation system 177 comprises a left side fan 107, a left side air intake 109, a left side on off switch 111, and an electrical power source. The purpose of the left side fan 107 is to draw air 300 in from the left side air intake 109, and pump the air into the left air tube 113. The left side air intake 109 is a small opening through which the air 300 entering the left side fan 107 flows. The left side fan 107 is controlled via a left side on/off switch 111. The left side fan 107 is powered by an electrical power source 155.

The left side fan 107, left side air intake 109, left side on/off switch 111, and the electrical power source 155 are mounted on the safety goggles 119. The left side fan 107, left side on/off switch 111, and the electrical power source 155 are commercially available. The left side air intake 109 is may be included as part of the left side fan 107 or may be formed directly into the safety goggles 119. The electrical power source 155 is being used to refer to at least one battery that is in wired connection between the left side on/off switch 111 and the left side fan 107.

The right side ventilation system 166 comprises a right side fan 108, a right side air intake 110, a right side on/off switch 112, and a second electrical power source 156. The purpose of the right side fan 108 is to draw the air 300 in from the right side air intake 110 and pump the air 300 into the right air tube 114. The right side air intake 110 is a small opening through which the air 300 entering the right side fan 108 flows. The right side fan 108 is controlled via the right side on-off switch 112. The right side fan 108 is powered via the second electrical power source 156. The second electrical power source 156 may be the same as or independent from the power source used to power the left side ventilation system. The second electrical power source 156 is being used to refer to at least one battery that is in wired connection between the right side on/off switch 112 and the right side fan 108.

The right side fan 108, the right side air intake 110, right side on/off switch 112, and the second electrical power source 156 are mounted on the safety goggles 119. The right side fan 108, right side on/off switch 112, and the second electrical power source 156 are commercially available. The right side air intake 110 may be included as part of the right side fan 108 or may be formed directly into the safety goggles 119.

Materials that are suitable for use in the left side air tube 113 include, but are not limited to, polycarbonate tubing, polyethylene tubing, polypropylene tubing and latex tubing. Alternatively, the left side shield 105, the right side shield 106, bridge 116, the top shield 104, the bottom shield 120, the left side air tube 113, and, when used, the left temple 117 and right temple 118 may be formed as a single unit.

The right side air tube 114 directs the flow of air from the right side fan 108 to the right lens 103 of the safety goggles 119. The right side air tube 114 is a conduit with a plurality small holes 121 formed along the right side air tube 114. A first end 137 of the right side air tube 114 is attached to the right side fan's 108 output. A second end 138 of the right side air tube 114 is positioned next to the right lens 103 such that the air flows out of the right side air tube 114 through the plurality of holes 121 on to the right lens 103. The plurality of holes 121 are formed in various sizes depending on each hole's specific position relative to the right lens 103. The purpose of varying the hole's size is to provide increased air flow to areas more prone to fogging.

The left side air tube 113 directs the flow of air from the left side fan 107 to the left lens 102 of the safety goggles 119. The left side air tube 113 is a conduit with a plurality small holes 121 formed along the left side air tube 113. A third end 139 of the left side air tube 113 is attached to the left side fan's 107 output. A fourth end 140 of the left side air tube 113 is positioned next to the left lens 102 such that the air flows out of the left side air tube 113 through the plurality of holes 121 on to the left lens 102. The plurality of holes 121 are formed in various sizes depending on each hole's specific position relative to the left lens 102. The purpose of varying the hole's size is to provide increased air flow to areas more prone to fogging.

Materials that are suitable for use in the left side air tube 113 and the right side air tube 114 include, but are not limited to, polycarbonate tubing, polyethylene tubing, polypropylene tubing and latex tubing. Alternatively, the left side shield 105, the right side shield 106, bridge 116, the top shield 104, the bottom shield 120, the left side air tube 113, the right side air tube 114, and, when used, the left temple 117 and right temple 118 may be formed as a single unit.

To use the invention 100, the wear first has to put on the safety goggles 119. Once put on, the users can turn on the left side on off 111 switch to operate the left side ventilation system 177 which turns on the left side fan 107 which pumps air into the space between the left lens 102 and the wearer 200. This airflow cools the space between the left lens 102 and the wearer and helps to remove any excess water vapor.

Similarly, the user can turn on the right side on off 112 switch to operate the right side ventilation system 166, which turns on the right side fan 108 which pumps air into the space between the right lens 103 and the wearer 200. This airflow cools the space between the right lens 103 and the wearer and helps to remove any excess water vapor. The ability to independently operate the left side ventilation system and the right side ventilation system is considered an important design feature of the invention 100.

With respect to the above description, it is to be realized that the optimum dimensional relationship for the various components of the invention described above and in FIGS. 1 through 6, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

Is shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. Protective eyewear safety goggles comprising:
a frame;
a left side ventilation system, a right side ventilation system, a left side air tube, and a right side air tube;
wherein the left side ventilation system and right side ventilation system are adapted to draw air in and circulate said air across a space formed between the frame and a left and a right eye of a wearer;
wherein the frame is further defined with a left lens, a right lens, a left side shield, a right side shield, and a bridge;
wherein the frame includes a top shield as well as a bottom shield;
wherein the left lens is adapted to protect a left eye of said wearer, the right lens is adapted to protect a right eye of the wearer, and the bridge is adapted to rest on a nose of the wearer; wherein the left side shield is adapted to protect the left eye from impacts and debris coming from the left side of the wearer; wherein the right side shield is adapted to protect the right eye from impacts and debris coming from the right side of the wearer; wherein the top shield is adapted to protect the left and the right eyes, from impacts and debris coming from above the wearer, and the bottom shield is adapted to protect the left and the right eyes from impacts and debris coming from below the wearer;
wherein the frame includes a strap, or a left temple and a right temple;
wherein the left side ventilation system comprises a left side fan, a left side air intake, a left side on off switch, and an electrical power source.

2. The protective eyewear according to claim 1 wherein the left side fan draws air in from the left side air intake, and directs said air into the left air tube; wherein the left side air intake is a small opening through which the air entering the left side fan flows.

3. The protective eyewear according to claim 2 wherein the left side fan is controlled via a left side on/off switch; wherein the left side fan is powered by the electrical power source.

4. The protective eyewear according to claim 3 wherein the left side fan, left side air intake, left side on/off switch, and the electrical power source are mounted on the safety goggles.

5. The protective eyewear according to claim 4 wherein the electrical power source is further defined as including at least one battery that is in wired connection between the left side on/off switch and the left side fan.

6. The protective eyewear according to claim 1 wherein the right side ventilation system comprises a right side fan, a right side air intake, a right side on/off switch, and a second electrical power source.

7. The protective eyewear according to claim 6 wherein the right side fan draws air in from the right side air intake and directs said air into the right air tube.

8. The protective eyewear according to claim 7 wherein the right side air intake is a small opening through which the air entering the right side fan flows.

9. The protective eyewear according to claim 8 wherein the right side fan is controlled via the right side on-off switch; wherein the right side fan is powered via the second electrical power source.

10. The protective eyewear according to claim 9 wherein the second electrical power source is further defined as including at least one battery that is in wired connection between the right side on/off switch and the right side fan.

11. The protective eyewear according to claim 10 wherein the right side air tube directs the flow of air from the right side fan to the right lens of the safety goggles; wherein the right side air tube is a conduit with a plurality small holes formed along the right side air tube; wherein a first end of the right side air tube is attached to the right side fan's output; wherein a second end of the right side air tube is positioned next to the right lens such that the air flows out of the right side air tube through the plurality of holes on to the right lens.

12. The protective eyewear according to claim 5 wherein the left side air tube directs the flow of air from the left side fan to the left lens of the safety goggles; wherein the left side air tube is a conduit with a plurality small holes formed along the left side air tube; wherein a third end of the left side air tube is attached to the left side fan's output; wherein a fourth end of the left side air tube is positioned next to the left lens such that the air flows out of the left side air tube through the plurality of holes on to the left lens.

* * * * *